United States Patent [19]

Howe et al.

[11] 4,336,389

[45] Jun. 22, 1982

[54] 2-SUBSTITUTED-4-ARYL-5-THIAZOLECAR- BOXYLIC ACIDS AND THEIR DERIVATIVES AS SAFENING AGENTS

[75] Inventors: Robert K. Howe, Bridgeton; Len F. Lee, Maryland Heights, both of Mo.

[73] Assignee: Monsanto Company, St. Louis, Mo.

[21] Appl. No.: 905,682

[22] Filed: May 15, 1978

[51] Int. Cl.³ .................. C07D 277/20; C07D 277/32; C07D 277/34

[52] U.S. Cl. ..................................... 548/201; 548/182; 548/188; 548/190; 548/198; 71/90; 71/118

[58] Field of Search ....................... 71/90; 260/302 R; 548/182, 201

[56] References Cited

U.S. PATENT DOCUMENTS

| | | | |
|---|---|---|---|
| 2,535,876 | 12/1950 | Stewart | 71/90 |
| 3,155,678 | 11/1964 | Hatchard | 71/90 |
| 3,506,679 | 4/1970 | Cavalla et al. | 260/302 R |
| 3,957,808 | 5/1976 | Miller et al. | 260/302 A |
| 4,115,095 | 9/1978 | Franz et al. | 71/90 |
| 4,144,047 | 3/1979 | Franz et al. | 71/90 |

OTHER PUBLICATIONS

Nakagawa et al., "Synthesis of sulfur—containing, etc;", (1970) CA 73 No. 109731 x (1970).
Lechat et al., "Comparison of the hypolipemic, etc;" (1971) CA 75 No. 108274 e (1971).
I.C.I., "Thiazole derivatives" (1967) CA 68 No. 68976 g (1968).
Csavassy et al., "Thiazole compounds, I, etc;" (1974) CA 81 No. 169464 n (1974).

*Primary Examiner*—Glennon H. Hollrah
*Attorney, Agent, or Firm*—Stanley M. Tarter; Howard C. Stanley

[57] ABSTRACT

These compounds have been found to be effective in reducing herbicidal injury to direct-seeded rice caused by 2-chloro-2',6'-diethyl-N-(butoxymethyl)acetanilide.

7 Claims, No Drawings

2-SUBSTITUTED-4-ARYL-5-THIAZOLECARBOXYLIC ACIDS AND THEIR DERIVATIVES AS SAFENING AGENTS

This invention relates to novel 2-substituted-4-aryl-5-thiazolecarboxylic acids and derivatives thereof as well as their use in compositions and methods for reducing herbicidal injury. More specifically, the invention relates to novel compositions and methods for reducing injury to direct-seeded rice by 2-chloro-2',6'-diethyl-N-(butoxymethyl)acetanilide (hereinafter referred to as butachlor) which comprises treating the rice plant locus or the seed of the rice plant with an effective amount of a 2-substituted-4-aryl-5-thiazolecarboxylic acid or derivative thereof that will be described more fully below.

BACKGROUND OF THE INVENTION

Butachlor is very useful for controlling weeds in the presence of growing crops, especially transplanted rice. Application of butachlor to direct-seeded rice at rates necessary to kill or stunt weeds, however, injures the rice plant, slowing growth and development. Accordingly, butachlor cannot be used for controlling weeds in the presence of direct-seeded rice. Obviously, a safening agent consisting of a chemical compound that could be used to treat either the seed of the rice plant, the rice plant locus, or the rice plant ifself, such that a reduction of injury due to application of the herbicide without a corresponding reduction of herbicidal action on the weed, would be quite beneficial.

DESCRIPTION OF THE INVENTION

In accordance with the novel aspects of the present invention, injury to rice due to application thereto of butachlor may be reduced without a corresponding reduction in injury to the weeds by application to the rice plant locus or the seed of the rice plant prior to planting of an effective amount of a safening agent comprising a 2-substituted-4-aryl-5-thiazolecarboxylic acid or derivative thereof having the formula

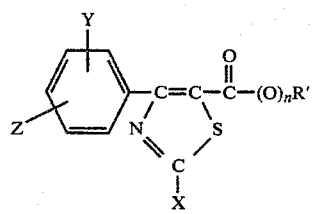

wherein n is zero or one; X is selected from the group consisting of halogen, lower alkoxy, phenoxy and halophenoxy; Y and Z are independently selected from the group consisting of hydrogen, halogen, trifluoromethyl, nitro and lower alkyl; when n is one, R' is hydrogen, alkyl having up to 6 carbon atoms or agriculturally accepted cations and when n is zero, R' is chloro.

As used herein, the term "lower alkyl" or "lower alkoxy" is understood to include alkyl or alkoxy groups having up to five carbon atoms, inclusive.

The term "alkyl" is understood to include branched, unbranched and cyclic alkyl groups.

"Halogen" includes bromine, chlorine, fluorine and iodine.

"Halophenoxy" is understood to mean phenoxy substituted by one or two halogen moieties.

The term "agriculturally acceptable cations" is understood to mean those cations that are commonly used to form the salt of the free acid. Such cations include, but are not limited to, alkali metal, alkaline earth, substituted amine and ammonium cations.

Safening agents useful in accordance with the present invention include, but are not limited to, ethyl 2-chloro-4-phenyl-5-thiazolecarboxylate; ethyl 2-chloro-4-m-trifluoromethylphenyl-5-thiazolecarboxylate; ethyl 2-chloro-4-p-fluorophenyl-5-thiazolecarboxylate; ethyl 2-chloro-4-p-chlorophenyl-5-thiazolecarboxylate; ethyl 2-chloro-4-o-chlorophenyl-5-thiazolecarboxylate; ethyl 2-chloro-4-m-tolyl-5-thiazolecarboxylate; ethyl 2-chloro-4-p-nitrophenyl-5-thiazolecarboxylate; ethyl 2-ethoxy-4-phenyl-5-thiazolecarboxylate; ethyl 2-ethoxy-4-m-trifluoromethylphenyl-5-thiazolecarboxylate; ethyl 2-(2',4'-dichlorophenoxy)-4-m-trifluoromethylphenyl-5-thiazolecarboxylate; 2-chloro-4-phenyl-5-thiazolecarboxylic acid; 2-chloro-4-m-trifluoromethylphenyl-5-thiazolecarboxylic acid; 2-chloro-4-phenyl-5-thiazolecarbonyl chloride; 2-chloro-4-p-chlorophenyl-5-thiazolecarboxylic acid; 2-chloro-4-p-chlorophenyl-5-thiazolecarbonyl chloride; methyl 2-chloro-4-phenyl-5-thiazolecarboxylate; methyl 2-chloro-4-p-chlorophenyl-5-thiazolecarboxylate; n-propyl 2-chloro-4-phenyl-5-thiazolecarboxylate; isopropyl 2-chloro-4-phenyl-5-thiazolecarboxylate; n-propyl 2-chloro-4-p-chlorophenyl-5-thiazolecarboxylate; sodium salt of 2-chloro-4-phenyl-5-thiazole-carboxylic acid; sodium salt of 2-chloro-4-p-chlorophenyl-5-thiazolecarboxylic acid; isopropylamine salt of 2-chloro-4-phenyl-5-thiazolecarboxylic acid; triethanolamine salt of 2-chloro-4-phenyl-5-thiazolecarboxylic acid.

Preferred are those safening agents of the foregoing formula in which X is halogen, especially chloro. Further preferred are those in which n is one and R' is lower alkyl, especially ethyl.

Generally, the 2-substituted-4-phenyl-5-thiazolecarboxylates of the foregoing formula may be prepared by either of two methods. If the desired compound is one in which X is halogen, especially chloro, the preparation utilized follows the following reaction scheme:

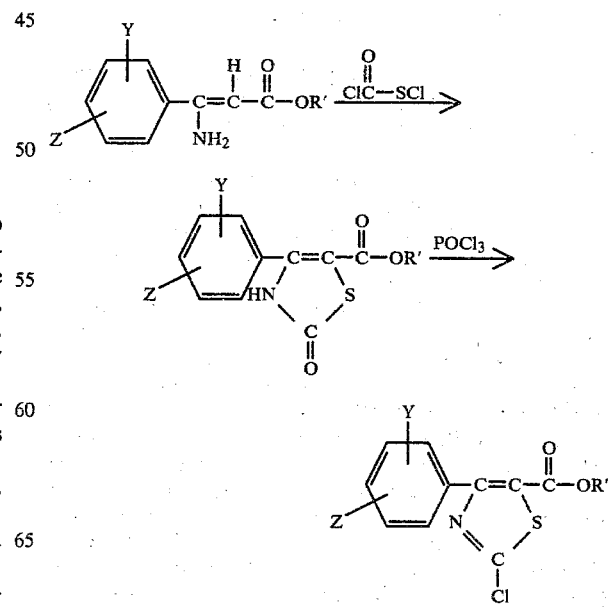

In accordance with the above scheme, β-amino-cinnamates prepared in accordance with literature procedures (Lukes et al, Collection Czechoslov, Chem. Commun., Volume 25, Page 607, 1960) was reacted with chlorocarbonylsulfenyl chloride and heated to about 100° C. Crystallization of the resulting mixture with petroleum ether yields the appropriate 4-aryl-2,3-dihydro-2-oxo-5-thiazolecarboxylate which may be converted to the appropriate 4-aryl-2-chloro-5-thiazolecarboxylate by reaction with excess phosphorus oxychloride held at reflux. Excess phosphorus oxychloride is removed under reduced pressure and the residue poured into ice water. Extraction with ether gives the desired product.

In order to more fully illustrate this procedure, the following examples are presented.

EXAMPLE 1

Preparation of Ethyl 2-Chloro-4-Phenyl-5-Thiazolecarboxylate

To a solution of 20.0 g (0.105 mole) of ethyl β-aminocinnamate in 40 ml. of chlorobenzene under ice cooling was added a solution of 11.6 g (0.112 mole) of chorocarbonylsulfenyl chloride in 10 ml. of chlorobenzene. The reaction mixture was heated at 110° C. for 2 hours, cooled to triturated with petroleum ether. The precipitate was heated with hot benzene, cooled and filtered to give 14.4 g (55%) of ethyl 2,3-dihydro-2-oxo-4-phenyl-5-thiazolecarboxylate as yellow needles. A mixture of 3.0 g (0.012 mole) of ethyl 2,3-dihydro-2-oxo-4-phenyl-5-thiazolecarboxylate and 14 ml. of phosphorus oxychloride was held at reflux for 24 hours and cooled. The reaction mixture was poured into ice water. The solid precipitate was extracted into ether. The ether solution was dried and concentrated under reduced pressure. The residue was recrystallized from hexane to give 2.2 g (68%) of ethyl 2-chloro-4-phenyl-5-thiazolecarboxylate, m.p. 56°-57° C.

Anal. Calc'd. for $C_{12}H_{10}ClNO_2S$: C, 53.83; H, 3.76; N, 5.23; Cl, 13.24; S, 11.98. Found: C, 53.86; H, 3.78; N, 5.21; Cl, 13.14; S, 11.98.

EXAMPLE 2

Preparation of Ethyl 2-Chloro-4-m-Trifluoromethylphenyl-5-thiazolecarboxylate To a solution of 14.4 g (0.119 mole) of ClCOSCl in 100 ml. of chlorobenzene was added a solution of 28.5 g (0.110 mole) of ethyl β-amino-m-trifluoromethylcinnamate (85% pure) in 20 ml. of chlorobenzene at 20°-25° C. The reaction mixture was stirred at 80° C. for 1 hour, cooled, and triturated with 100 ml. of petroleum ether (30°-75° C.). The precipitate was collected to give 16.7 g of yellow needles, m.p. 167°-170° C., which were recrystallized from benzene to give 13.5 g (39%) of ethyl 2,3-dihydro-2-oxo-4-(m-trifluoromethylphenyl)-5-thiazolecarboxylate as yellow needles, m.p. 168°-171° C. A mixture of 8.0 g (0.0253 mole) of ethyl 2,3-dihydro-2-oxo-4-(m-trifluoromethylphenyl)-5-thiazolecarboxylate, 30 ml. of POCl₃ was heated to reflux for 60 hours. Excess POCl₃ was removed under reduced pressure and the black residue was treated with 100 ml. of water. The aqueous mixture was extracted twice with 100 ml. of ether. The combined ether extracts were dried over MgSO₄ and concentrated under reduced pressure to give 9.6 g of black oil which was chromatographed on 180 g of silica gel. After the earlier fractions were removed, the fractions, eluted with 600 ml. of hexane-ether (4:1 v/v), contained 5.7 g (67%) of oil, which solidified after standing, m.p. 26.5°-27° C.

Anal. Calc'd. for $C_{13}H_9ClF_6NO_2S$: C, 46.50; H, 2.70; N, 4.17; Cl, 10.56. Found: C, 46.61; H, 2.71; N, 4.19; Cl, 10.70.

An alternate procedure for preparing the 2-halo-4-aryl-5-thiazolecarboxylates of the invention encompasses the reaction of a substituted benzoylacetate with sulfuryl chloride to prepare 2-chloro-benzoylacetate which may be converted to 2-amino-4-aryl-5-thiazolecarboxylates by reaction with thiourea in ethanol at reflux. Ethanol is then removed under reduced pressure and the residue neutralized with sodium bicarbonate solution to give a 2-amino-4-aryl-5-thiazolecarboxylic acid ester. A solution of said ester in appropriate acid is diazotized at −5° to 30° C. with sodium nitrite. The resulting diazonium salt solution is poured into the corresponding cuprous halide or potassium iodide solution. After gas evolution had subsided, the reaction mixture is extracted with ether. The ether extract is dried and concentrated and the residue is purified by either Kugelrohr distillation at reduced pressure or by chromatography.

For purposes of clarification, the following reaction scheme and examples are provided.

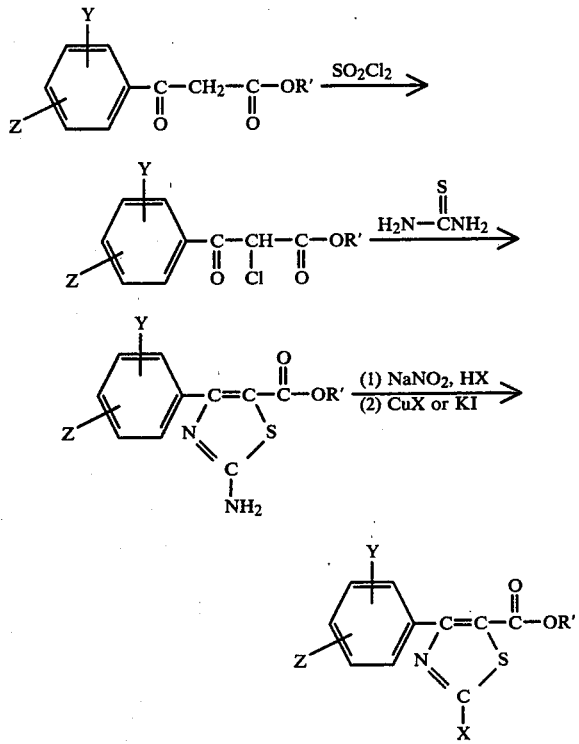

EXAMPLE 3

Preparation of Ethyl 2-Chloro-4-(p-Fluorophenyl)-5-Thiazolecarboxylate

A mixture of 10.5 g (0.05 mole) of ethyl p-fluorobenzoylacetate, 6.7 g (0.05 mole) of sulfuryl chloride and 30 ml. of chloroform was held at reflux for 18 hours and cooled. The chloroform solution was washed with water, dried (MgSO₄) and concentrated under reduced pressure. The residue was distilled to give 10.8 g (88%) of ethyl 2-chloro-(p-fluoro)-benzoylacetate as an oil. A mixture of 10.8 g (0.0441 mole) of ethyl 2-chloro-(p-fluoro)benzoylacetate, 3.36 g (0.0441 mole) of thiourea, 20 ml. of water and 10 ml. of ethanol was held at reflux for 3 hours. Ethanol was removed under reduced pressure. The residue was made basic with saturated sodium bicarbonate. The solid was filtered, washed with water and recrystallized from ethanol to give 8.9 g (76%) of ethyl 2-amino-4-(p-fluorophenyl)-5-thiazolecarboxylate as white prisms, m.p. 205°–208° C. To 4.0 g (0.015 mole) of ethyl 2-amino-4-(p-fluorophenyl)-5-thiazolecarboxylate was added 30 ml. of concentrated hydrochloric acid and 30 ml. of glacial acetic acid. The carboxylate did not dissolve completely. To this mixture was added 30 ml. of chloroform. The carboxylate dissolved gradually into the chloroform solution. the reaction mixture was cooled to 0°–5° C. with an ice bath. To the above mixture was added with vigorous stirring 4.0 g (0.058 mole) of sodium nitrite. The reaction mixture was stirred at 5°–10° C. for 30 minutes and poured into a solution of 1.48 g (0.0150 mole) of cuprous chloride in 20 ml. of concentrated hydrochloric acid. After the gas evolution subsided, the reaction mixture was diluted with water. The chloroform layer was separated and the aqueous layer was extracted with chloroform. The combined chloroform solution was washed with water followed by saturated sodium bicarbonate, dried (MgSO$_4$) and concentrated under reduced pressure. The residual solid was recrystallized from ethanol to give 3.3 g (77%) of ethyl 2-chloro-4-(p-fluorophenyl)-5-thiazolecarboxylate as orange needles, m.p. 113°–114° C.

Anal. Calc'd. for $C_{12}H_9ClFNO_2S$: C, 50.44; H, 3.17; N, 4.90. Found: C, 50.42; H, 3.18; N, 4.90.

EXAMPLE 4

Preparation of Ethyl 2-Chloro-4-p-Chlorophenyl-5-Thiazolecarboxylate

To a cold (5° C.) vigorously stirred mixture of 121.87 g (0.936 mole) of ethyl acetoacetate, 314 ml. of benzene and 626 ml. of water was added 41.25 ml. of 33% sodium hydroxide. To the above mixture was added simultaneously in two dropping funnels 177.0 g (1.01 mole) of p-chlorobenzoyl chloride and 188.8 ml. of 33% sodium hydroxide in 2 hours. The reaction mixture became pasty. The reaction mixture was heated at 35° C. for 1 hour, cooled and filtered to give 170.0 g of sodium salt of ethyl 2-benzoylacetoacetate. Part (150 g) of this salt was added to a mixture of 39.0 g (0.729 mole) of ammonium chloride and 78 ml. of concentrated ammonium hydroxide in 780 ml. of water. The mixture was stirred at 40°–50° C. for 3 hours and cooled in an ice bath. The precipitate was filtered to give 115.5 g of yellow solid which was Kugelrohr distilled to give 76.0 g (38% based on ethyl acetoacetate) of crude ethyl p-chlorobenzoylacetate. A mixture of 40.0 g (0.175 mole) of crude ethyl p-chlorobenzoylacetate, 24.2 g (0.18 mole) of sulfuryl chloride and some chloroform was held at reflux for 6 hours, cooled and concentrated to give 49.0 g of crude ethyl 2-chloro-p-chlorobenzoylacetate. A mixture of 46.0 g (0.174 mole) of crude ethyl 2-chloro-p-chlorobenzoylacetate, 13.25 g (0.174 mole) of thiourea, and 174 ml. of ethanol was held at reflux for 2 hours and cooled. The precipitate was filtered and neutralized with saturated sodium bicarbonate. The insoluble material was filtered to give 37.0 g (80%) of ethyl 2-amino-4-p-chlorophenyl-5-thiazolecarboxylate, m.p. 198°–200° C. To a cold (−5° C.) mixture of 11.3 g (0.04 mole) of ethyl 2-amino-4-p-chlorophenyl-5-thiazolecarboxylate and 80 ml. of 85% phosphonic acid was added 40 ml. of 70% nitric acid. To the above mixture was added with vigorous stirring, 4.0 g (0.0434 mole) of sodium nitrite in 20 minutes at −5°–0° C. The reaction mixture was stirred at −5°–0° C. for 10 minutes and poured into a mixture of 4.0 g (0.04 mole) of cuprous chloride, 20 ml. of concentrated hydrochloric acid and 20 ml. of water. The reaction mixture was stirred at room temperature for 30 minutes, after which time evolution had subsided. The precipitate was filtered to give 10.5 g of solid which was Kugelrohr distilled (145° C. at 0.05 mm Hg) to give 6.0 g of solid, m.p. 113°–120° C., which was recrystallized from hot ethanol to give 4.4 g (37%) of ethyl 2-chloro-4-p-chlorophenyl-5-thiazolecarboxylate as a white solid, m.p. 119°–120° C.

Anal. Calc'd. for $C_{12}H_9Cl_2NO_2S$: C, 47.70; H, 3.00; N, 4.64. Found: C, 47.71; H, 2.97; N, 4.55.

EXAMPLE 5

Preparation of Ethyl 2-Chloro-4-(o-Chlorophenyl)-5-Thiazolecarboxylate

To a cold (5° C.) mixture at 55.0 g (0.423 mole) of ethyl acetoacetate, 70 ml. of benzene, 18.3 ml. of 33% sodium hydroxide, and 141 ml. of water was added simultaneously with vigorous stirring 80.0 g (0.457 mole) of o-chlorobenzoyl chloride and 76 ml. of 33% sodium hydroxide in 1 hour as described in Example 4. The aqueous solution of sodium salt of ethyl o-chlorobenzoylacetoacetate was stirred with 22.5 g (0.424 mole) of ammonium chloride for 18 hours. The aqueous solution was then saturated with 25.0 g of sodium chloride. At this moment, some precipitate formed which was filtered. The analysis indicated this material was mainly the sodium salt of ethyl o-chlorobenzoylacetoacetate. The sodium salt and the aqueous filtrate were combined and acidified with dilute hydrochloric acid. The oil which separated was extracted with ether. The ether solution was dried (MgSO$_4$) and concentrated under reduced pressure. The residue was Kugelrohr distilled to give 30.0 g of oil which contained mainly ethyl o-chlorobenzoylacetoacetate. This material was stirred with a mixture of 7.2 g of ammonium chloride, 14 ml. of concentrated ammonium hydroxide and 150 ml. of water and worked up as described in Example 4 to give 16.6 g (15%) of crude ethyl o-chlorobenzoylacetate which was about 92% pure. A mixture of 15.0 g (0.065 mole) of ehtyl o-chlorobenzoylacetate, 9.5 g (0.070 mole) of sulfuryl chloride and 20 ml. of chloroform was held at reflux for 6 hours and concentrated to give 17.3 g of crude ethyl 2-chloro-o-chlorobenzoylacetate. A mixture of 17.0 g (0.065 mole) of ethyl 2-chloro-o-chlorobenzoylacetate, 4.94 g (0.065 mole) of thiourea and 65 ml. of ethanol was held at reflux for 2 hours and worked up as described in Example 4 to give 15.0 g of solid, m.p. 114°–136° C. which was recrystallized twice from ethanol to give 5.8 g (31%) of ethyl 2-amino-4-(o-chlorophenyl)-5-thiazolecarboxylate, m.p. 162°–164° C. Part (1.0 g) of this material was recrystallized from toluene to give 0.75 g of pure ethyl 2-amino-4-(o-chlorophenyl)-5-thiazolecarboxylate, m.p. 165°–166° C. A solution of 4.2 g (0.015 mole) of ethyl 2-amino-4-(o-chlorophenyl)-5-thiazolecarboxylate in 50 ml. of 85% phosphoric acid and 15 ml. of nitric acid was diazotized with 1.12 g (0.016 mole) of sodium nitrite as described in Example 4. The diazonium salt solution was poured into a solution of 1.50 g (0.015 mol) of cuprous chloride in 7.5 ml. of concentrated hydrochloric acid and 7.5 ml. of water. The reaction mixture was worked up as described in Example 4 to give 4.0 g of oil which was Kugelrohr distilled (150° C. at 0.3 mm) to give 2.0 g of oil. The material was purified to give 0.66 g (15%) of ethyl 2-chloro-4-(o-chlorophenyl)-5-thiazolecarboxylate as a colorless liquid.

Anal. Calc'd. for $C_{12}H_9Cl_2NO_2S$: C, 47.69; H, 3.00; N, 4.63; Cl, 23.43. Found: C, 47.61; H, 3.02; N, 4.62; Cl, 23.45.

EXAMPLE 6

Preparation of Ethyl 2-Chloro-4-(m-Tolyl)-5-Thiazolecarboxylate

To a cold (5° C.) mixture of 137.5 g (1.05 mole) of ethyl acetoacetate, 175 ml. of benzene, 325 ml. of water, and 45.8 ml. of 33% sodium hydroxide was added simultaneously 221.05 g (1.430 mole) of m-toluoyl chloride and 190 ml. of 33% sodium hydroxide as described in Example 4. The aqueous solution of sodium salt of ethyl m-toluoylacetoacetate was stirred with 56.3 g of ammonium chloride overnight and worked up as described in Example 4 to give 38.0 g (17%) of crude ethyl m-toluoylacetate after a Kugelrohr distillation (95°–98° C. at 0.05 mm Hg). A mixture of 20.6 g (0.1 mole) of crude ethyl m-toluoylacetate, 13.6 g (0.105 mole) of sulfuryl chloride, and 30 ml. of chloroform was held at reflux for 6 hours and worked up as described in Example 4 to give 25.0 g of ethyl 2-chloro-m-toluoylacetate, which was used directly as described below. A mixture of 22.5 g (0.1 mole) of ethyl 2-chloro-m-toluoylacetate, 7.6 g (0.1 mole) of thiourea and 100 ml. of ethanal was held at reflux for 2 hours and worked up as described in Example 4 to give 23.0 g of solid, which was recrystallized from ethanol to give 11.6 g (44%) of ethyl 2-amino-4-(m-tolyl)-5-thiazolecarboxylate, m.p. 185°–187° C. An additional 4.5 g (17%) of less pure ethyl 2-amino-4-(m-tolyl)-5-thiazolecarboxylate, m.p. 183°–184° C. was obtained by concentration of the mother liquor. To a cold (−5° C.) mixture of 10.5 g (0.04 mole) of ethyl 2-amino-4-(m-tolyl)-5-thiazolecarb and 80 ml. of 85% phosphoric acid was added 40 ml. of 70% nitric acid. To the vigorously stirred above mixture was added 3.0 g (0.0434 mole) of sodium nitrite in 20 minutes. The reaction mixture was stirred for 10 minutes and poured into a mixture of 4.0 g (0.04 mole) of cuprous chloride, 20 ml. of concentrated hydrochloric acid and 20 ml. of water. After the gas evolution had subsided the reaction mixture was extracted with ether, dried (MgSO4) and concentrated under reduced pressure to give 10 g of oil which was Kugelrohr distilled (135°–140° C. at 0.05 mm) to give 6.5 g of oil, which was crystallized from ethanol to give 3.9 g (34%) of the desired product as a white solid, m.p. 41°–42° C.

Anal. Calc'd. for $C_{13}H_{12}ClNO_2S$: C, 55.42; H, 4.29; N, 4.97; Cl, 12.58. Found: C, 55.38; H, 4.33; N, 4.99; Cl, 12.53.

EXAMPLE 7

Preparation of Ethyl 2-Chloro-4-(p-Nitrophenyl)-5Thiazolecarboxylate

Ethyl 2-chloro-p-nitrobenzoylacetate, obtained from ethyl p-nitrobenzoylacetate and sulfuryl chloride in accordance with the procedure of Balog et al, *Studio. Univ. Bebes. Boylai.*, Vol. 1, No. 2, Page 155 (1960), was converted to ethyl 2-amino-4-p-nitrophenyl-5-thiazolecarboxylate with thiourea in accordance with a procedure in the above-mentioned publication. To a cooled (15° C.) solution of 10.0 g (0.0334 mole) of ethyl 2-amino-4-(p-nitrophenyl)-5-thiazolecarboxylate in 100 ml. of concentrated HCl and 100 ml. of glacial HOAc was added 7.0 g (0.101 mole) of NaNO2 in 15 minutes. The reaction mixture was stirred for 10 minutes and poured into a solution of 3.78 g (0.038 mole) of CuCl in 60 ml. of concentrated HCl. A slow gas evolution occurred which was accelerated when 50 ml. of water was added to the reaction mixture. The reaction mixture gradually turned yellow with precipitation of white solid. The precipitate was extracted with CHCl3. The CHCl3 solution was dried (MgSO4) and concentrated under reduced pressure. The residue was boiled with hot MeOH and filtered. The solid was recrystallized from acetone-chloroform to give 2.4 g of the desired product, m.p. 146°–148° C.

Anal. Calc'd. for $C_{12}H_9ClN_2O_4S$: C, 46.09; H, 2.90; N, 8.95; Cl, 11.34. Found: C, 46.08; H, 2.92; N, 8.95; Cl, 11.23.

The analogues in which X is lower alkoxy, phenoxy or halophenoxy are prepared by treating the corresponding 2-chloro compound with sodium alkoxide or potassium phenoxide. Sodium alkoxide, such as sodium ethoxide, may be prepared from sodium and dried ethanol. The reaction mixture containing sodium alkoxide and the appropriate 2-chloro compound is stirred for a long period of time and poured into dilute hydrochloric acid. The organic layer is extracted with ether. The ether solution is dried, and concentrated and the residue is Kugelrohr distilled at reduced pressure (2 mm) to give ethyl 2-ethoxy-4-phenyl-5-thiazolecarboxylate or ethyl 2-ethoxy-4-(m-trifluoromethylphenyl)-5-thiazolecarboxylate.

EXAMPLE 8

Preparation of Ethyl 2-Ethoxy-4-Phenyl-5-Thiazolecarboxylate

To a solution of NaOC2H5, prepared from 1.8 g (0.0783 g atom) of Na and 25 ml. of dry ethanol (dried from Mg (OEt)2) was added 4.0 g (0.0149 mole) of Example 1. The reaction mixture was stirred at room temperature under N2 for 20 hours and poured into 50 ml. of ice cold 6 NHCl. The mixture was extracted twice with 50 ml. of ether. The ether extracts were dried (MgSO4) and concentrated under reduced pressure. The residue was distilled on a Kugelrohr at 2 mm (140°–170° C.) to give 3.55 g (86%) of the desired product as white solid, m.p. 32°–34° C.

Anal. Calc'd. for $C_{14}H_{15}NO_3S$: C, 60.63; H, 5.45; N, 5.05. Found: C, 60.62; H, 5.46; N, 5.06.

EXAMPLE 9

Preparation of Ethyl 2-Ethoxy-4-(m-Trifluoromethylphenyl)-5-Thiazolecarboxylate To a NaOC2H5 solution, preparation from 0.5 g (0.217 g atom) of Na and 25 ml. of dry ethanol was added 1.0 g (0.00298 mole) of Example 2. The solution was stirred at room temperature for 16 hours and poured into 50 ml. of 6 N HCl. The mixture was extracted twice with 50 ml. of ether. The combined ether solution was washed with saturated NaHCO3, dried (MgSO4) and concentrated under reduced pressure. The residue was chromatographed on 20 g of silica gel using ether-petroleum ether (1:5 v/v) as eluant. The first 300 ml. eluant was concentrated under reduced pressure and the residue was distilled on a Kugelrohr at 2 mm (temperature 140°–170° C.) to give 0.65 g (63%) of the desired product as white solid, m.p. 69°–72° C.

Anal. Calc'd. for $C_{15}H_{14}F_3NO_3S$: C, 52.17; H, 4.09; N, 4.06. Found: C, 52.12; H, 4.08; N, 4.09.

EXAMPLE 10

Preparation of Ethyl 2-(2',4'-Dichlorophenoxy)-4-(m-Trifluoromethylphenyl)-5-Thiazolecarboxylate A mixture of 3.68 g (0.0110 mole) of ethyl 2-chloro-4-m-trifluoromethylphenyl-5-thiazolecarboxylate, 1.96 g (0.0120 mole) of 2,4-dichlorophenyl, 1.66 g (0.012 mole) of $K_2CO_3$ and 50 ml. of acetone was held at reflux for 22 hours. Acetone was removed under reduced pressure. The residue was treated with 50 ml. of water and extracted with 100 ml. of ether. The ether solution was washed successively with 50 ml. of $NaHCO_3$, 30 ml. of 10% NaOH and 50 ml. of water, dried ($MgSO_4$) and concentrated under reduced pressure. The residue was recrystallized twice from hexane to give 4.1 g (81%) of the desired product as white needles, m.p. 72°–73° C.

Anal. Calc'd. for $C_{19}H_{12}F_3Cl_2NO_2S$: C, 49.36; H, 2.62; N, 3.03; Cl, 15.34. Found: C, 49.32; H, 2.62. N, 3.04; Cl, 15.40.

Various esters may be prepared by reaction of the corresponding acid chloride and the appropriate alcohol. The acid chloride is prepared by reaction of the free acid with thionyl chloride.

Salts may be prepared by reaction of the free acid with the appropriate base.

EXAMPLE 11

Preparation of 2-Chloro-4-Phenyl-5-Thiazolecarboxylic Acid

A mixture of 53.4 g (0.2 mole) of ethyl 2-chloro-4-phenyl-5-thiazolecarboxylate, 8.0 g (0.2 mole) of NaOH, 200 ml. of water and 400 ml. of tetrahydrofuran was stirred for 16 hours and extracted with ether. The organic layer was discarded. The aqueous layer was made acidic and the precipitate was collected and air-dried to give 43.2 g (90%) of the desired product, m.p. 170°–171° C.

Anal. Calc'd. for $C_{10}H_6ClNO_2S$: C, 50.11; H, 2.52; N, 5.84. Found: C, 50.06; H, 2.55; N, 5.84.

EXAMPLE 12

Preparation of 2-Chloro-4-Phenyl-5-Thiazolecarbonyl Chloride

A mixture of 40.6 g (0.17 mole) of 2-chloro-4-phenyl-5-thiazolecarboxylic acid and 100 ml. of thionyl chloride was heated on a steam bath for 6 hours and concentrated under reduced pressure to give 38.0 g (88%) of the acid chloride as a white solid, m.p. 53°–55° C.

Anal. Calc'd. for $C_{10}H_5Cl_2NOS$: C, 46.53; H, 1.95; N, 5.43. Found: C, 46.45; H, 1.99; N, 5.41.

EXAMPLE 13

Preparation of Methyl 2-Chloro-4-Phenyl-5-Thiazolecarboxylate

A mixture of 5.16 g (0.02 mole) of the compound of Example 12 and 40 ml. of methanol was held at reflux for 1 hour and concentrated under reduced pressure. The residual solid was stirred with ether. The ether solution was washed with saturated sodium bicarbonate, dried ($MgSO_4$), and concentrated under reduced pressure to give 3.1 g (61%) of the desired product as a white solid, m.p. 55°–57° C.

Anal. Calc'd. for $C_{11}H_8ClNO_2S$: C, 52.07; H, 3.17; N, 5.52. Found: C, 52.02; H, 3.21; N, 5.50.

EXAMPLE 14

Preparation of n-Propyl 2-Chloro-4-Phenyl-5-Thiazolecarboxylate

A mixture of 5.16 g (0.02 mole) of the compound of Example 12 and 40 ml. of n-propanol was held at reflux for 7 hours and concentrated under reduced pressure. The residual waxy material (6.09 g) was stirred with ether and filtered to give 1.0 g of solid, m.p. 155°–156° C. The ether solution was washed with saturated sodium bicarbonate, dried ($MgSO_4$), and concentrated under reduced pressure to give 3.5 g of waxy material which was heated with hexane and filtered. The hexane filtrate was concentrated under reduced pressure to give 2.1 g of oil which was dissolved in ether. The ether solution was washed with 10% sodium hydroxide solution, dried ($MgSO_4$) and concentrated under reduced pressure to give 1.8 g of oil which was Kugelrohr distilled to give 1.4 g (25%) of the desired product as a colorless oil; $n_D^{25} = 1.5868$.

Anal. Calc'd. for $C_{13}H_{12}ClNO_2S$: C, 55.41; H, 4.29; N, 4.97. Found: C, 55.35; H, 4.30; N, 4.95.

In accordance with the novel aspects of the present invention, the 2-substituted-4-aryl-5-thiazolecarboxylic acids and derivatives thereof are useful for reducing herbicidal injury to rice plants. The amount of safening agent employed in the method and compositions of the invention will vary depending upon the manner of application, rate of application, environmental factors as well as other factors known in the art. In each instance, the amount employed is a safening effective amount, i.e., the amount which reduces crop injury by the herbicide.

The safening agent may be applied to the plant locus in a mixture with the herbicide or it may be applied directly to the rice seed itself. By application to the "plant locus" is meant application to the plant growing medium, such as the soil, as well as the seeds, emerging seedlings, roots, stems, leaves, flowers, fruits or other plant parts.

To illustrate the effectiveness of the 2-substituted-4-aryl-5-thiazolecarboxylic acids and derivatives thereof, the following examples are presented. These examples are presented merely as being illustrative of the novel aspects of the invention and are not intended to be a limitation as to the scope thereof.

EXAMPLE 15

A good grade of top soil is placed in a container and compacted to a depth of approximately 1.27 cm. from the top of said container. A predetermined number of rice seeds to be tested are placed on top of the soil. A quantity of soil sufficient to substantially fill the container is measured and placed in a second container. A measured quantity of the safening agent dispersed or dissolved in a suitable carrier is applied to the soil in the second container. A measured quantity of butachlor dispersed or dissolved in a suitable carrier is then sprayed on the soil already treated with the safening agent. The soil containing the safening agent and herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and herbicide and the pans are leveled. The pans are then placed on a sand bench in the greenhouse and watered from below as needed. The plants are observed at the end of approximately 21 days and the results in terms of percent inhibition of each seed lot are recorded. For each test series a pan of plants is also prepared containing no herbicide and no safening agent as a control. Additionally, for each test, a pan of plants is prepared with soil covering the seed containing no herbicide and only the measured amount of safening agent being incorporated into the soil covering the seeds to ascertain any herbicidal effect of the safening agent alone. For each series of tests the herbicidal effect of the herbicide is observed from pans of plants treated with the same quantity of herbicide alone. The "safening effect" is determined by adding the hericidal effect of the herbicide when applied alone to the herbicidal effect of the safening agent when applied alone (in no instance, however, will this sum be greater than 100) and substracting from that the herbicidal effect obtained when the herbicide and safening agent are incorporated into the soil as discussed above.

Table I summarizes the results obtained when the compounds of the invention were tested in accordance with the procedure of Example 15.

TABLE I

| Safening Agent (Compound of Example Number) | Rate of Safening Agent (kg/h) | Rate of Herbicide (kg/h) | Safening Effect |
| --- | --- | --- | --- |
| 1 | 8.96 | 4.48 | 75 |
| 8 | 8.96 | 4.48 | 75 |
| 9 | 8.96 | 4.48 | 20 |
| 2 | 8.96 | 4.48 | 50 |
| 11 | 8.96 | 4.48 | 50 |
| 12 | 8.96 | 4.48 | 50 |
| 13 | 8.96 | 4.48 | 30 |
| 14 | 8.96 | 4.48 | 20 |
| 7 | 8.96 | 4.48 | 25 |
| 3 | 8.96 | 6.72 | 65 |
| 4 | 8.96 | 6.72 | 85 |
| 6 | 8.96 | 6.72 | 65 |
| 5 | 8.96 | 6.72 | 65 |
| 10 | 8.96 | 4.48 | 43 |

EXAMPLE 16

A good grade of top soil is placed in a plastic pot. A measured quantity of the safening agent dispersed or dissolved in a suitable carrier is sprayed on the soil surface. A measured quantity of butachlor herbicide dissolved in a solvent is sprayed on the soil surface. Presoaked rice is seeded into the pots that were previously flooded with water and the water level lowered below the soil surface for one week. The pots are flooded at least up to the soil surface for the duration of the test. The plants are observed at the end of approximately 21 days and the results in terms of the percent inhibition of rice is recorded. As in Example 15, for each test pots are prepared containing soil treated only with butachlor. For each test, pots are also prepared containing soil treated only with the safening agent. Pots are also prepared in which the soil is not treated with either the herbicide or the safening agent. The safening effect is determined in accordance with Example 15.

Table II summarizes the results obtained when the compounds of the invention were tested in accordance with the procedure of Example 16.

TABLE II

| Safening Agent (Compound of Example Number) | Rate of Safening Agent (kg/h) | Rate of Herbicide (kg/h) | Safening Effect** |
| --- | --- | --- | --- |
| 1 | 1.12 | 0.14 | 78 |
|   | 1.12 | 0.56 | 99 |
| 2 | 0.56 | 0.07 | 68 |
|   | 0.56 | 0.28 | 26 |
|   | 0.56 | 1.12 | * |
| 11 | 0.56 | 0.07 | * |
|   | 0.56 | 0.28 | 63 |
|   | 0.56 | 1.12 | 45 |
| 12 | 0.56 | 0.07 | 35 |
|   | 0.56 | 0.28 | 80 |
|   | 0.56 | 1.12 | 62 |
| 10 | 0.56 | 0.07 | * |
|   | 0.56 | 0.28 | * |
|   | 0.56 | 1.12 | * |
| 7 | 0.56 | 0.07 | * |
|   | 0.56 | 0.28 | 38 |
|   | 0.56 | 1.12 | * |
| 3 | 0.56 | 0.07 | 30 |
|   | 0.56 | 0.28 | 73 |
|   | 0.56 | 1.12 | 62 |
| 4 | 0.56 | 0.07 | 30 |
|   | 0.56 | 0.28 | 70 |
|   | 0.56 | 1.12 | 32 |

*Safening effect between 0 and 20
**Mean of two replicates

EXAMPLE 17

5.08 cm. of a good grade of top soil is placed in a 7.62 cm. deep plastic pot. A predetermined number of barnyard grass seeds are applied to the soil surface. A measured quantity of the safening agent dispersed or dissolved in a suitable carrier is sprayed on the soil surface. A measured quantity of butachlor herbicide dissolved in a solvent is sprayed on the soil surface. Pre-soaked rice is seeded into the pots that were previously flooded with water. The water level is lowered below the soil surface for one week to allow barnyard grass to emerge. The pots are flooded just above the soil surface for the duration of the test. The plants are observed at the end of approximately 21 days and the results in terms of percent inhibition recorded. For each test, pots are prepared containing soil treated only with butachlor. For each test, pots are prepared containing soil treated only with the safening agent. Pots are also prepared containing untreated soil. Table II represents the results of tests conducted in accordance with the procedure of Example 17.

TABLE III

| Safening Agent (Compound of Example Number) | Rate of Safening Agent (kg/h) | Rate of Herbicide (kg/h) | Inhibition* Rice | Barnyard Grass |
| --- | --- | --- | --- | --- |
| — | — | 0.07 | 31 | 99 |
| — | — | 0.28 | 74 | 100 |
| — | — | 1.12 | 98 | 100 |
| 3 | 0.07 | — | 0 | 0 |
| 3 | 0.07 | 0.07 | 0 | 97 |
| 3 | 0.07 | 0.28 | 5 | 99 |
| 3 | 0.07 | 1.12 | 70 | 100 |
| 3 | 0.28 | — | 0 | 0 |
| 3 | 0.28 | 0.07 | 0 | 92 |
| 3 | 0.28 | 0.28 | 5 | 100 |
| 3 | 0.28 | 1.12 | 58 | 100 |
| 3 | 1.12 | — | 0 | 0 |
| 3 | 1.12 | 0.07 | 0 | 92 |
| 3 | 1.12 | 0.28 | 0 | 100 |
| 3 | 1.12 | 1.12 | 43 | 100 |

TABLE III-continued

| Safening Agent (Compound of Example Number) | Rate of Safening Agent (kg/h) | Rate of Herbicide (kg/h) | Inhibition* Rice | Inhibition* Barnyard Grass |
| --- | --- | --- | --- | --- |
| 4 | 0.07 | — | 0 | 0 |
| 4 | 0.07 | 0.07 | 0 | 99 |
| 4 | 0.07 | 0.28 | 0 | 100 |
| 4 | 0.07 | 1.12 | 78 | 100 |
| 4 | 0.28 | — | 0 | 0 |
| 4 | 0.28 | 0.07 | 0 | 99 |
| 4 | 0.28 | 0.28 | 0 | 99 |
| 4 | 0.28 | 1.12 | 40 | 100 |
| 4 | 1.12 | — | 0 | 0 |
| 4 | 1.12 | 0.07 | 0 | 99 |
| 4 | 1.12 | 0.28 | 0 | 99 |
| 4 | 1.12 | 1.12 | 28 | 100 |

*Mean of two replicates

EXAMPLE 18

5.08 cm. of a good grade of top soil is placed in a 7.62 cm. deep plastic pot. A predetermined number of barnyard grass seeds are applied to the soil surface. A measured quantity of the safening agent and butachlor dispersed or dissolved in a suitable carrier is applied to the soil surface. Pre-soaked rice is seeded into the pots that were previously flooded with water. The water level is lowered below the soil surface for one week. The pots are flooded just above the soil surface for the duration of the test. The plants are observed at the end of approximately 21 days and the results in terms of percent inhibition recorded. For each test, pots are prepared containing soil treated only with butachlor. For each test, pots are prepared containing soil treated only with the safening agent. Pots are also prepared with untreated soil. Table IV represents the results of tests conducted in accordance with the procedure of Example 18.

TABLE IV

| Safening Agent (Compound of Example Number) | Rate of Safening Agent (kg/h) | Rate of Herbicide (kg/h) | % Inhibition* Rice | % Inhibition* Barnyard Grass |
| --- | --- | --- | --- | --- |
| — | — | 0.07 | 64 | 100 |
| — | — | 0.28 | 78 | 100 |
| — | — | 1.12 | 100 | 100 |
| 8 | 1.12 | — | 0 | 0 |
| 8 | 1.12 | 0.07 | 30 | 100 |
| 8 | 1.12 | 0.28 | 88 | 100 |
| 8 | 1.12 | 1.12 | 95 | 100 |
| Ethyl 2-(2',4'-dichlorophenoxy)-4-phenyl-5-thiazolecarboxylate | 1.12 | — | 0 | 0 |
| Ethyl 2-(2',4'-dichlorophenoxy)-4-phenyl-5-thiazolecarboxylate | 1.12 | 0.07 | 15 | 83 |
| Ethyl 2-(2',4'-dichlorophenoxy)-4-phenyl-5-thiazolecarboxylate | 1.12 | 0.28 | 88 | 98 |
| Ethyl 2-(2',4'-dichlorophenoxy)-4-phenyl-5-thiazolecarboxylate | 1.12 | 1.12 | 99 | 100 |
| Triethanolamine salt of 2-chloro-4-phenyl-5-thiazolecarboxylate | 1.12 | — | 0 | 0 |
| Triethanolamine salt of 2-chloro-4-phenyl-5-thiazolecarboxylate | 1.12 | 0.07 | 0 | 88 |
| Triethanolamine salt of 2-chloro-4-phenyl-5-thiazolecarboxylate | 1.12 | 0.28 | 20 | 99 |
| Triethanolamine salt of 2-chloro-4-phenyl-5-thiazolecarboxylate | 1.12 | 1.12 | 60 | 100 |
| 4 | 0.07 | — | 0 | 0 |
| 4 | 0.07 | 0.07 | 5 | 90 |
| 4 | 0.07 | 0.28 | 63 | 100 |
| 4 | 0.07 | 1.12 | 88 | 100 |
| 4 | 0.28 | — | 0 | 0 |
| 4 | 0.28 | 0.07 | 0 | 85 |
| 4 | 0.28 | 0.28 | 30 | 100 |
| 4 | 0.28 | 1.12 | 40 | 100 |
| 4 | 1.12 | — | 0 | 0 |
| 4 | 1.12 | 0.07 | 0 | 85 |
| 4 | 1.12 | 0.28 | 30 | 100 |
| 4 | 1.12 | 1.12 | 88 | 100 |

*Mean of two replicates

EXAMPLE 19

5.08 cm. of a good grade of top soil is placed in a 7.62 cm. deep plastic pot. A predetermined number of weed seeds and rice seeds are applied to the soil surface. Butachlor and ethyl 2-chloro-4-phenyl-5-thiazolecarboxylate are applied to a soil cover layer as a mixture and incorporated by shaking the treated soil cover layer in a plastic bag. The cover layers were then placed on the pre-seeded pots. The plants are observed at the end of approximately 21 days and the results in terms of percent inhibition recorded. For each test, pots are prepared containing soil treated only with butachlor. For each test, pots are prepared containing soil treated only with the safening agent. Pots are also prepared with untreated soil. Table V represents the results of tests conducted in accordance with the procedure of Example 19.

TABLE V

| Rate of Herbicide (kg/h) | Rate of Safening Agent (kg/h) | Barnyard Grass | Crabgrass | Panicum | Foxtail | Rice |
| --- | --- | --- | --- | --- | --- | --- |
| 2.24 | — | 100 | 100 | 99 | 100 | 50 |
| 4.48 | — | 100 | 100 | 100 | 100 | 78 |
| 8.96 | — | 100 | 100 | 100 | 100 | 93 |
| — | 8.96 | 0 | 0 | 0 | 0 | 0 |
| 2.24 | 8.96 | 100 | 100 | 100 | 100 | 8 |
| 4.48 | 8.96 | 100 | 100 | 100 | 100 | 43 |
| 8.96 | 8.96 | 100 | 100 | 100 | 100 | 45 |

The above examples illustrate that the thiazolecarboxylates of the present invention are useful in reducing herbicidal injury to rice plants. The safening agents may be applied to the plant locus as a mixture, i.e., a mixture of a herbicidally effective amount of butachlor and a safening effective amount of safening agent, or sequentially, i.e., the plant locus may be treated with an effective amount of butachlor followed by a treatment with the safening agent or vice versa. The ratio of butachlor to safening agent may vary depending upon various factors, such as the weeds to be inhibited, mode of application, etc., but normally a herbicide to safening agent ratio ranging from 1:25 to 25:1 (preferably 1:5 to 5:1) parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixtures thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixtures thereof in a liquid or particulate soli form can be carried out by conventional techniques utilizing, for example, spreaders, power dusters, boom and hand sprayers, spray dusters and granular applicators. The compositions can also be applied from airplanes as a dust or spray. If desired, application of the compositions of the invention to plants can be accomplished by incorporating the compositions in the soil or other media.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

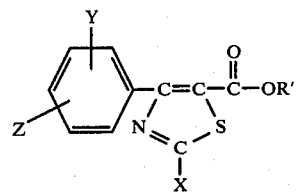

wherein X is selected from the group consisting of halogen, lower alkoxy, phenoxy and halophenoxy; Y and Z are independently selected from the group consisting of hydrogen, halogen, trifluoromethyl, nitro and lower alkyl; and R' is hydrogen, lower alkyl or agriculturally acceptable cations.

2. A compund according to claim 1 wherein X is halogen.

3. A compound according to claim 2 wherein X is chloro.

4. A compound according to claim 1 wherein R' is lower alkyl.

5. A compound according to claim 4 wherein R' is ethyl.

6. A compound according to claim 1 wherein Y is chloro and Z is hydrogen.

7. A compound according to claim 6 which is ethyl 2-chloro-4-p-chlorophenyl-5-thiazolecarboxylate.

* * * * *